United States Patent [19]

Merger et al.

[11] Patent Number: 4,686,302

[45] Date of Patent: * Aug. 11, 1987

[54] SIMULTANEOUS PREPARATION OF NITRILES AND ACRYLAMIDE OR METHACRYLAMIDE

[75] Inventors: Franz Merger, Frankenthal; Wolfgang Schwarz, Pfinztal, both of Fed. Rep. of Germany

[73] Assignee: BASF Aktiengesellschaft, Fed. Rep. of Germany

[ * ] Notice: The portion of the term of this patent subsequent to Jan. 6, 2004 has been disclaimed.

[21] Appl. No.: 677,036

[22] Filed: Nov. 30, 1984

[30] Foreign Application Priority Data

Dec. 2, 1983 [DE] Fed. Rep. of Germany ....... 3343673

[51] Int. Cl.$^4$ .................. C07C 120/00; C07C 102/08
[52] U.S. Cl. ................................... 558/314; 564/127; 564/204; 260/404
[58] Field of Search .................. 260/465.1, 465.9, 464, 260/465.2, 465 A; 558/314; 564/127, 204

[56] References Cited

U.S. PATENT DOCUMENTS

| | | | |
|---|---|---|---|
| 2,417,024 | 3/1947 | Tuerck et al. | 260/465.9 |
| 3,734,942 | 5/1973 | Dennis | 260/465.2 X |
| 3,836,567 | 9/1974 | Krekler et al. | 260/465.2 X |
| 3,928,274 | 12/1975 | Chakrabarti | 260/294.9 |
| 4,365,092 | 12/1982 | Harwell | 564/135 |
| 4,408,079 | 10/1983 | Merger et al. | 568/463 |

FOREIGN PATENT DOCUMENTS

| | | |
|---|---|---|
| 0058927 | 5/1984 | European Pat. Off. . |
| 1643722 | 6/1971 | Fed. Rep. of Germany . |
| 2057986 | 6/1971 | Fed. Rep. of Germany . |
| 2310184 | 9/1974 | Fed. Rep. of Germany . |
| 0128302 | 10/1977 | Japan . |
| 1334859 | 10/1973 | United Kingdom . |

OTHER PUBLICATIONS

Houben-Weyl; Methoden der Organischen Chemie, 8, pp. 325-330, (1952), "Sauerstoffverbindungen III".
Field et al.; J.A.C.S.; 83, (1961), pp. 1983-1987.
Leusink et al.; Rec. des Trav. Chim. des Pays-Bas, 96, (1977), pp. 142-145.
Leusink et al.; Rec. des. Trav. Chim. des Pays-Bas, 95, (1976), pp. 123-125.
Patai (Editor) & Rappoport; "The Chemistry of the Cyano Group", (1970), pp. 92-96.
Hydrocarbon Process., 41 (11), (1962), pp. 187-190.
Houben-Weyl, "Methoden der Organischen Chemie", 1014, (1968), pp. 55-66.
Houben-Weyl, "Methoden der Organischen Chemie", 8, (1962), p. 235.

Primary Examiner—Joseph Paul Brust
Attorney, Agent, or Firm—Keil & Weinkauf

[57] ABSTRACT

Nitriles of the general formula I $$R^1-CN \qquad (I)$$

where $R^1$ is a saturated or unsaturated, straight-chain, branched or cyclic alkyl radical, an aralkyl radical or an aryl radical, each of which is of not more than 20 carbon atoms and can be unsubstituted or further substituted, and (meth)acrylamide are prepared simultaneously by a process in which an aldoxime of the general formula III $$R^1-CH=NOH \qquad (III)$$

where $R^1$ has the above meanings, is heated at from 50° to 180° C. in the presence of a copper(II) carboxylate and of (meth)acrylonitrile.

6 Claims, No Drawings

SIMULTANEOUS PREPARATION OF NITRILES AND ACRYLAMIDE OR METHACRYLAMIDE

The present invention relates to a novel process for the simultaneous preparation of nitriles and acrylamide or methacrylamide, starting from the oximes of the particular aldehydes and acrylonitrile or methacrylonitrile.

The literature discloses a large number of processes for the preparation of nitriles; for example DE-A-2 310 184 proposes the conversion of carboxamides to the corresponding nitriles by means of phosgene. However, because phosgene has to be handled, this process is particularly expensive.

Specific nitriles, such as acrylonitrile or aromatic nitriles, can be prepared by ammonoxidation of propene or propane or of the corresponding alkylaromatics (Hydrocarbon Process. 41 (11) (1962), 187, DE-B-2 057 986 and DE-A-1 643 722). However, the preparation of methacrylonitrile according to this principle is not very satisfactory, and the ammoxidation of higher olefins is unknown.

The dehydration of the readily obtainable aldoximes to nitriles has also been described (Houben-Weyl, Methoden der organischen Chemie, 8, page 325 et seq.). The most frequently used water-eliminating compound is acetic anhydride, but this causes side reactions in the case of acid-sensitive compounds, and can in some cases also have an acylating action.

Because sulfur dioxide and hydrogen chloride are formed, thionyl chloride is not suitable for this purpose for technical reasons; moreover, it also tends to undergo side reactions.

Other dehydrating agents, eg. cyanuric chloride (U.S. Pat. No. 3,928,274), are only used in a few special cases.

It is an object of the present invention to provide a process which can be used to synthesize a large number of nitriles in a simple manner and without technically very complicated apparatus.

The water produced during the dehydration of the aldoximes to the nitriles combines with the particular dehydrating agents to give, in general, relatively large amounts of useless waste products; it is therefore a further object of the present invention to prepare further useful products, in addition to the nitriles, by using suitable water-accepting reactants.

We have found that this object is achieved, and that nitriles of the general formula I $$R^1-CN \qquad (I)$$

where $R^1$ is a saturated or unsaturated, straight-chain, branched or cyclic alkyl radical, an aralkyl radical or an aryl radical, each of which is of not more than 20 carbon atoms and can be unsubstituted or further substituted, and acrylamides of the general formula II $$CH_2=C-CONH_2 \\ \phantom{CH_2=C-}| \\ \phantom{CH_2=C-}R^2 \qquad (II)$$

where $R^2$ is hydrogen or methyl, are obtained simultaneously and in an advantageous manner, if an aldoxime of the general formula III $$R^1-CH=NOH \qquad (III)$$

where $R^1$ has the above meanings, is heated at from 50° to 180° C. in the presence of a copper(II) carboxylate obtained from a carboxylic acid of 2 to 18 carbon atoms, and in the presence of an acrylonitrile of the general formula IV $$CH_2=C-CN \\ \phantom{CH_2=C-}| \\ \phantom{CH_2=C-}R^2 \qquad (IV)$$

where $R^2$ has the above meanings.

The process according to the invention is carried out using oximes derived from aldehydes of the general formula VI $$R^1-CHO \qquad (VI)$$

where $R^1$ is a saturated or unsaturated, straight-chain, branched or cyclic alkyl radical, an aralkyl radical or an aryl radical, each of which is of not more than 20 carbon atoms. This radical can be substituted by further groups which are inert under the reaction conditions, for example by halogen or lower alkoxy (also in the geminal position), lower acyloxy, lower alkoxycarbonyl or lower mono- or dialkylamino groups.

Examples of such aldehydes are acetaldehyde, propionaldehyde, acrolein, butyraldehyde, 3-methylbut-2-enal, 2-methylpentanal, 2-ethylhexanal, citronellal, citral, 2-phenylpropanal, benzaldehyde, 4-methylbenzaldehyde, 4-chlorobenzaldehyde, 4-methoxybenzaldehyde and 4-dimethylaminobenzaldehyde.

The novel process is preferably carried out using aldoximes of the general formula V $$CH_2=C-CH=NOH \\ \phantom{CH_2=C-}| \\ \phantom{CH_2=C-}R^3 \qquad (V)$$

where $R^3$ is a straight-chain, branched or cyclic alkyl radical of 2 to 15 carbon atoms which can be unsubstituted or further substituted. Examples of suitable further substituents are the abovementioned groups.

The aldoximes of the general formula V are derived from the particular alpha-alkyl-substituted acroleins. Examples of such acroleins are alpha-ethylacrolein, alpha-butylacrolein, alpha-(2-ethylhexyl)-acrolein, alphanonylacrolein, alpha-cyclohexylacrolein, alpha-(4-methylcyclohexyl)-acrolein, alpha-(3-carbethoxypropyl)-acrolein and alpha-(4,4-dimethylaminobutyl)-acrolein.

The preparation of the stated aldehydes is carried out by a conventional method and is unimportant with regard to the invention.

The aldoximes which are suitable for the process according to the invention can be prepared from the particular aldehydes and hydroxylammonium salts, likewise by a conventional method, as described in, for example, Houben-Weyl, Methoden der organischen Chemie, Volume 10/4, page 55 et seq.

The novel process is carried out at from 50° to 180° C., preferably from 75° to 150° C., in particular from 100° to 140° C.

The reaction is carried out in general under atmospheric pressure, but in some cases it is advantageous to employ superatmospheric pressure of not more than 20 bar.

The procedure can be carried out in the absence of a solvent, but is preferably carried out in the presence of an inert solvent, such as toluene, xylene, mesitylene, chlorobenzene, nitrobenzene, tetralin, decalin, dioxane, dibutyl ether or n-butyl acetate.

The novel simultaneous preparation of nitriles and acrylamide or methacrylamide is carried out in the presence of a copper(II) carboxylate which is derived from a carboxylic acid of 2 to 18, preferably 4 to 12, in particular 6 to 10, carbon atoms.

Suitable acids of this type are unsubstituted or substituted carboxylic acids containing a saturated or unsaturated straight-chain, branched or cyclic alkyl radical, aralkanoic acids, oxaalkanoic acids and aromatic carboxylic acids, eg. acetic acid, propionic acid, alpha-chloropropionic acid, isobutyric acid, 2-methylbutanoic acid, 2-ethylhexanoic acid, 3,5,5-trimethylhexanoic acid, decenoic acid, 9-dodecenoic acid, 9-octadecenoic acid, cyclohexanecarboxylic acid, phenylacetic acid, 1-phenylcyclopentane-1-carboxylic acid, methoxyacetic acid, benzoic acid, 3,5-dichlorobenzoic acid or naphthoic acid.

The copper salts required for the novel process can be prepared by a conventional method, for example by reacting the carboxylic acids with copper(II) carbonate, or by reacting a copper salt with an alkali metal or ammonium salt of the particular carboxylic acid.

The amount of copper(II) carboxylate used is from 0.1 to 10, preferably from 0.1 to 5, in particular from 0.5 to 1.5, mol %, based on 1 mole of aldoxime.

In the process according to the invention, acrylonitrile or methacrylonitrile (see above, general formula IV) also has to be present.

Acrylonitrile or methacrylonitrile is used in an amount of from 150 to 500, preferably from 150 to 300, mol %, based on 1 mole of aldoxime.

Under these conditions, the aldoxime used is converted to the desired nitrile in good yields (as high as 95% of theory); at the same time, an amount of the acrylonitrile or methacrylonitrile added which corresponds to the amount of the oxime is converted virtually quantitatively to the particular acrylamide.

The process according to the invention is usually carried out as follows: the copper(II) carboxylate and acrylonitrile or methacrylonitrile, preferably in an inert solvent, are heated to the stated temperature, after which the particular aldoxime is added. The procedure can be carried out either batchwise or continuously.

When the reaction is complete, the desired product, ie. acrylamide or methacrylamide (see above, general formula II), is first isolated by crystallization. Usually, the acrylonitrile or methacrylonitrile added is recovered in the form of the amide, in an amount of about 95-100 mol %, based on the oxime. The resulting solution containing the other desired product (nitrile) is then freed from the solvent and excess acrylonitrile or methacrylonitrile.

After the catalyst has been washed out with water, the resulting nitriles are sufficiently pure for many intended uses. However, they can also be purified further by fractional distillation or, if desired, can be freed from traces of copper by ion exchange.

The acrylamide or methacrylamide, which is the desired product, can also be used directly for many purposes, but can likewise be purified further (recrystallization, ion exchange).

Using the novel process, even those nitriles which are usually difficult to synthesize can be prepared in a simple manner.

The nitriles obtained by the process according to the invention are useful intermediates, for example for the synthesis of drugs and dyes or for the preparation of modifiable polymers, eg. for dispersions and surface coatings.

One of the uses of acrylamide is as a starting material for copolymers. Methacrylamide is used as, for example, a comonomer, mainly in the production of dispersions.

The Examples which follow illustrate the invention.

EXAMPLE 1

A solution of 132.5 g of acrylonitrile and 2 g of copper(II) acetate in 320 g of o-xylene was heated to the boil (92° C.), after which 85 g of methacrolein oxime were added dropwise in the course of 15 minutes, the temperature increasing to 108° C. After cooling to room temperature, the reacted mixture was analyzed by gas chromatography, using an internal standard. This showed that the solution contained 63 g (94%) of methacrylonitrile, 84.4 g of acrylonitrile and 61.8 g (96%, based on acrylonitrile converted) of acrylamide.

EXAMPLE 2

A solution of 382 g of acrylonitrile and 25.2 g of copper(II) 2-ethylhexanoate in 1800 g or o-xylene was heated to the boil (92° C.), after which 375 g of 95% pure alpha-ethylacrolein oxime were added dropwise in the course of 50 minutes, the temperature increasing to 110° C. Stirring was continued for a further 15 minutes, the mixture was allowed to cool and the precipitated acrylamide was filtered off under suction. Fractional distillation of the mother liquor gave 260 g (89%) of alpha-ethylacrylonitrile of boiling point 112° C.

EXAMPLE 3

A solution of 80.7 g of acrylonitrile and 5.3 g of copper(II) 2-ethylhexanoate in 250 g or o-xylene was heated to the boil (97° C.), after which 151.5 g of 99% pure alpha-nonylacrolein oxime were added dropwise in the course of 15 minutes, the temperature increasing to 115° C. during the addition. When the addition was complete, refluxing was continued for a further 10 minutes, after which the reaction mixture was cooled to −8° C. and the precipitated acrylamide was filtered off under suction. Fractional distillation of the mother liquor gave 121 g (89%) of alpha-nonylacrylonitrile of boiling point 122°–124° C./ 12 mbar.

EXAMPLE 4

A solution of 123 g of 95% pure hydroxypivalaldoxime in 100 g of o-xylene was added dropwise, in the course of 8 minutes, to a boiling solution of 106 g of acrylonitrile and 7 g of copper(II) 2-ethylhexanoate in 410 g of o-xylene, the temperature increasing from 96° C. to 115° C. Stirring was continued for a further 10 minutes at 115° C., the mixture was cooled to −14° C. and the precipitated acrylamide was separated off. Fractional distillation gave 82 g (83%) of hydroxypivalonitrile of boiling point 95°–97° C./15 mbar.

EXAMPLE 5

A mixture of 130 g of acrylonitrile and 2.3 g of copper(II) 2-ethylhexanoate was heated to the boil (75° C.), after which 43 g of methoxypivaldoxime were added dropwise in the course of 10 minutes, the temperature increasing to 83° C. When the addition was complete, stirring was continued for 10 minutes without heating, and the mixture was then cooled to room temperature. The excess acrylonitrile was distilled off, 250 ml of petroleum ether were added to the residue from the distillation, and the mixture was cooled to −5° C. The precipitated acrylamide was filtered off under suction, and the mother liquor was evaporated down under reduced pressure. Distillation of the residue gave 31.5 g (85%) of methoxypivalonitrile of boiling point 158°–160° C.

EXAMPLE 6

A solution of 74.2 g of acrylonitrile and 4.9 g of copper(II) 2-ethylhexanoate in 250 g of o-xylene was heated to the boil (92° C.), after which 84.7 g of benzaldoxime were added dropwise in the course of 20 minutes. When the addition was complete, stirring was continued for a further 10 minutes, the mixture was then cooled to −5° C. and the precipitated acrylamide was filtered off under suction. Fractional distillation of the mother liquor gave 63.5 g (88%) of benzonitrile of boiling point 73° C./20 mbar.

EXAMPLE 7

A solution of 53 g of acrylonitrile and 1.0 g of copper-(II) acetate in 100 g of o-xylene was heated to the boil (85° C.), after which a solution of 82 g of p-dimethylaminobenzaldoxime in 110 g of o-xylene was added dropwise by heating further. During the addition, the boiling point of the reaction mixture increased to 135° C. The mixture was stirred under reflux for a further 30 minutes and was then left to cool. The precipitated acrylamide was filtered off under suction, and the mother liquor was extracted by shaking with a little water. The organic phase was evaporated down and the residue was taken up in 400 ml of petroleum ether. After the mixture had been left to stand overnight at 0° C., 66 g (90%) of p-dimethylaminobenzonitrile were obtained in the form of yellow crystals of melting point 75°–76° C.

EXAMPLE 8

A solution of 28 g of alpha-(1-phenylethyl)acrolein oxime in 10 g of o-xylene was added dropwise, in the course of 6 minutes, to a boiling solution of 17 g of acrylonitrile and 0.38 g of copper(II) butyrate in 60 g of o-xylene. When the strongly exothermic reaction had died down, the mixture was cooled to room temperature and the acrylamide which had crystallized out was filtered off under suction. The mother liquor was diluted with 100 ml of diethyl ether and extracted with twice 50 ml of water. The organic phase was dried over magnesium sulfate and then evaporated down in a rotary evaporator, and the residue was fractionally distilled to give 22.6 g (90%) of alpha-(1-phenylethyl)-acrylonitrile of boiling point 63°–65° C./0.05 mbar.

We claim:

1. A process for the simultaneous parparation of a nitrile of the formula I $$R^1—CN \qquad (I)$$

where $R^1$ is a straight-chain or a branched-chain alkyl radical, or is a straight-chain or a branched-chain alkenyl radical, or is a cycloalkyl radical, or is an aralkyl radical or is an aryl radical, each of which is of not more than 20 carbon atoms and which radicals can be further substituted by halogen, lower alkoxy, lower alkoxycarbonyl or lower mono- or dialkylamino or $R^1$ is a 4-methylphenyl radical or a $HOCH_2C(CH_3)_2$— radical or a $CH_2=C(R_3)$— radical, where $R_3$ is cyclic alkyl, or 1-phenylethyl; and an acrylamide of the formula II

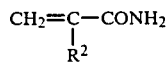

where $R^2$ is hydrogen or methyl, wherein an aldoxime of the formula III $$R^1—CH=NOH \qquad (III)$$

where $R^1$ has the above meanings, with the proviso that $R^1$ can not be ethenyl when $R^2$ is hydrogen, is heated at from 50° to 180° C. in the presence of a copper(II) carboxylate obtained from a straight-chain or a branched-chain alkanoic acid, or a straight-chain or a branched-chain alkenoic acid, or a cycloalkyl carboxylic acid, or an aralkanoic, oxaalkanoic or aromatic carboxylic acid, where the aryl groups are hydrocarbyl, or alpha chloropropionic acid, or 1-phenylcyclopentane-1-carboxylic acid, or methoxyacetic acid, or 3,5-dichlorobenzoic acid, said carboxylates being a total of 2 to 18 carbon atoms; and in the presence of an acrylonitrile of the formula IV

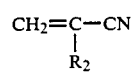

where $R^2$ has the above meanings.

2. The process of claim 1, wherein the reaction is carried out at from 75° to 150° C.

3. The process of claim 1, wherein the reactin is carried out in the presence of a copper(II) carboxylate obtained from a carboxylic acid of 4 to 12 carbon atoms.

4. The process of claim 1, wherein the reaction is carried out in the presence of an inert solvent.

5. The process of claim 1, wherein the reaction is carried out in the presence of from 150 to 500 mol %, based on the oxime, of an acrylonitrile of the formula IV

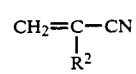

where $R^2$ has the meanings stated in claim 1.

6. The process of claim 1, wherein the carboxylate is obtained from acetic acid, propionic acid, alpha-chloropropionic acid, isobutyric acid, 2-methylbutanoic acid, 2-ethylhexanoic acid, 3,5,5-trimethylhexanoic acid, decenoic acid, 9-dodecenoic acid, 9-octadecenoic acid, cyclohexanecarboxylic acid, phenylacetic acid, 1-phenylcyclopentane-1-carboxylic acid, methoxyacetic acid, benzoic acid, 3,5-dichlorobenzoic acid or naphthoic acid.

* * * * *